United States Patent [19]

Wong et al.

[11] Patent Number: 4,691,714

[45] Date of Patent: Sep. 8, 1987

[54] RHEOLOGICAL TESTING APPARATUS AND METHOD

[75] Inventors: Jacob Y. Wong, Santa Barbara; Pierre Khuri-Yakub, Palo Alto; M. Ed Motamedi, Thousand Oaks; Marcus Y. Wong, Pacific Palisades, all of Calif.

[73] Assignees: Adamtek Corporation, Santa Barbara; Hibshman Corporation, San Luis Obispo, both of Calif. ; a part interest

[21] Appl. No.: 850,077

[22] Filed: Apr. 8, 1986

Related U.S. Application Data

[63] Continuation of Ser. No. 661,226, Oct. 15, 1984, abandoned.

[51] Int. Cl.⁴ .................................... A61B 10/00
[52] U.S. Cl. .................................... 128/738; 73/54; 73/570
[58] Field of Search ............... 128/632, 637, 660, 736, 128/738; 73/1 R, 1 G, 29, 32 R, 32 A, 54, 61.2, 64.1, 73, 570, 590, 335, 336.5; 374/117; 310/313 R, 313 B

[56] References Cited

U.S. PATENT DOCUMENTS

| | | |
|---|---|---|
| 3,844,273 | 10/1974 | Polson . |
| 3,844,276 | 10/1974 | McDougall . |
| 3,979,945 | 9/1976 | Kopito et al. . |
| 3,982,423 | 9/1976 | Schuster . |
| 3,986,388 | 10/1976 | Stolzy . |
| 4,117,716 | 10/1978 | Simon . |
| 4,224,949 | 9/1980 | Scott et al. . |
| 4,247,758 | 1/1981 | Rodrian . |
| 4,249,418 | 2/1981 | Ebata .................................. 374/117 |
| 4,387,724 | 6/1983 | Zartman . |
| 4,399,441 | 8/1983 | Vaughan et al. ............... 128/736 X |

Primary Examiner—Kyle L. Howell
Assistant Examiner—Francis J. Jaworski
Attorney, Agent, or Firm—Lyon & Lyon

[57] ABSTRACT

The device electronically measures fluid viscosity and temperature simultaneously principally for determining the changes in the properties of cervical mucus at the onset of ovulation. Interdigital transducers are used to generate and detect surface and bulk acoustic waves on one side of a slab of fused quartz. The change of phase of surface acoustic waves and the change in amplitude of doubly-reflected bulk acoustic waves are used to detect respectively the temperature and viscosity of fluid sample deposited on the opposite face of the slab.

24 Claims, 11 Drawing Figures

RHEOLOGICAL TESTING APPARATUS AND METHOD

This application is a continuation of application Ser. No. 661,226, filed Oct. 15, 1984, now abandoned.

BACKGROUND OF THE INVENTION

1. Field of the Invention

The present invention relates to an apparatus and method for determining rheological properties of biological and other liquids. The method and apparatus of the present invention is used to determine the viscosity and elastic properties of cervical mucus for women and other female mammals. For humans, the determination of the properties of the mucus is used to predict and indicate the inception and the presence of ovulation for increasing likelihood of conception or for contraception. For livestock and other mammals, the determination is used to detect estrus for breeding management.

2. Description of the Prior Art

Many forms of family planning require a woman wanting to avoid pregnancy to identify her fertile period so she can practice sexual abstinence or use other means of birth control during this period. On the other hand, marginally fertile couples desiring pregnancy have a higher probability of conceiving if sexual intercourse is confined to the female fertile period or if the couples abstain for several days before the period. Ovulation is the key event in the female fertile period. The fertile period consists of only about four days in the female menstrual cycle: three days preceding ovulation (necessitated by sperm survival), and one day after ovulation (necessitated by ovum survival).

It is well known that the rheology of cervical mucus undergoes significant changes at the onset and throughout the female fertile period. See Schuster, U.S. Pat. No. 3,982,423 (1976). During the immediate pre-ovulatory phase and the rest of the menstrual cycle, the mucus becomes less abundant and no longer possesses certain threadability characteristics. In rheological terms the mucus is highly viscous except during the ovulation phase of the menstrual cycle. If one can determine the changes in the viscoelastic properties of cervical mucus that occur before the onset of ovulation, it is possible to pinpoint the female fertile period.

In the so-called Billings method of contraception by periodic abstinence, a woman is taught to identify the precise characteristics of cervical mucus produced at various states of her menstrual cycle and their relationship to her fertile and infertile days. The method tends to be subjective and lacks quantitative precision so it tends to be unreliable. The more widely practiced Basal body temperature method uses the changes in daily temperature taken immediately at awakening to identify the temperature shift that occurs at or shortly after ovulation. To be effective the woman must adhere to a highly repetitive routine before the daily temperature taking because any restlessness, motion, infection or mental stress causes small temperature shifts, which can result in incorrect data. The Sympto-Thermal method charts temperature changes and changes in volume and viscosity of cervical mucus and teaches women to recognize such subjective symptoms of ovulation as inter-menstrual pain. This method fares no better because the measurements lack precision and objectivity.

Kopito, U.S. Pat. No. 3,979,945 (1976) and the aforementioned Schuster patent both teach devices designed to give quantitative measurements of rheological properties of cervical mucus, but both are complex and difficult to use and are mechanical devices subject to error. The mucus is not tested in situ.

Detecting estrus in cattle is important but is difficult for the farmer. Failure to detect estrus at the proper time means delayed breeding and long calving intervals, which result in a decreased production of milk and beef. The problem is further complicated as herd size increases because it is difficult to observe more cows. Various techniques have been advanced for the detection of estrus in cattle. For example, Scott, U.S. Pat. No. 4,224,949 (1980), and McDougall, U.S. Pat. No. 3,844,276 (1974), tests electrical resistance of cervical mucus using a bovine vaginal probe. Rodrian, U.S. Pat. No. 4,247,758 (1981), measures movements of animals which are said to be increased during estrus. Zartman, U.S. Pat. No. 4,387,724 (1983), measures long-term deep body temperature. None of these techniques utilizes the changes in rheological parameters such as viscosity for bovine cervical mucus at the onset and throughout the bovine estrus period.

OBJECTIVES OF THE INVENTION

A main object of the present invention is to disclose and provide a viscosity testing device, which is especially useful in testing the viscosity of cervical mucus. A further object of the invention is to create a device that is simple to operate and gives a quantitative, essentially error-free reading to note the viscosity changes in the mucus. A further object of the present invention is to disclose and provide a reliable device for testing the viscosity of cervical mucus of simple construction that functions electronically without moving parts in an inert apparatus in which the woman or animal is not exposed to electrical hazards. A further object of the present invention is to disclose and provide a device for measuring the viscosity of cervical mucus that also can read the temperature of the mucus so that both temperature and viscosity changes can be noted.

SUMMARY OF THE INVENTION

The present invention comprises the novel design of a device for the simultaneous measurement of the viscosity and temperature for biological and other fluids. In one preferred embodiment this invention takes the form of a vaginal probe with the sensing element located near its tip for the in-situ measurement of both the viscosity and temperature of the cervical mucus near the cervical os inside the vaginal cavity of the female mammal. The sensing element consists of zinc oxide (ZnO) interdigital transducers (IDTs) fabricated on one side of a fused quartz slab together with associated electronic circuits. Part of the circuits are located inside the probe cavity and the rest electrically connected to a remote box.

The IDTs are configured to generate and detect both surface and bulk acoustic waves on one side of the slab in such a way that the change in phase of the surface acoustic waves and the change in amplitude of the doubly-reflected bulk acoustic waves are used to detect respectively the temperature and the viscosity of fluid samples deposited on the opposite face of the same slab.

DESCRIPTION OF INVENTION AND OPERATING PRINCIPLES

The sensing element of the present invention is a device having a slab, preferably of fused quartz, with a first face exposable to the fluid of which the viscosity is to be tested. A bulk wave transmission means is fabricated on a second face of the slab for generating a bulk acoustic wave (BAW) toward the first face. A receiving transducer is fabricated on the slab in the path of the bulk wave after it reflects twice from the first face for receiving the reflected bulk wave from the first face and generating a first output. The viscosity of the fluid in contact with the first face controls the amplitude of the first output. A circuit attached to the receiving transducer measures the amplitude of the first output and compares the first output to a reference output. The reference output, for example, is one that would be obtained from a viscosity measurement of air in contact with the first face. By comparing the first output with the reference output, the viscosity can be determined.

The generating means also generates a surface acoustic wave (SAW) along the surface of the second face of the slab. The receiving transducer is positioned for receiving the surface acoustic wave and generating a second output. A second portion of the circuit receives a signal from the receiving transducer to measure the phase of the second output and to compare the second output to a second reference output indicative of normal temperature. The second output and the second reference output are compared, and the difference is a function of the temperature of the slab. Because the fluid sample is in good thermal contact with the slab, the slab temperature gives the fluid sample temperature indirectly.

The invention in one form is a safe plastic vaginal probe with the small quartz slab located near the tip for in situ measurement of both the viscosity and temperature of the cervical mucus inside the vaginal cavity near the cervical os.

In one embodiment, both the generator and the receiving transducers are interdigital transducers (IDT), a series of uniform metal electrodes in the form of two interspaced combs deposited onto the second face of the slab, which is covered by a piezoelectric film. When an electrical potential of the appropriate frequency is applied between the two metal combs, acoustic waves are excited and made to propagate on the surface and in the bulk of the substrate.

In the past, surface acoustic wave generators have been made using this design, but the bulk acoustic waves were discarded as unwanted. The present invention uses these bulk acoustic waves. As the waves change upon reflection from the outer face of the quartz depending on the viscosity of the fluid in contact with the face, the reflected waves received by the receiving transducer are indicative of changes in the viscosity of the fluid.

Preferably both the acoustic wave generator and receiver are on one side of the thin fused quartz slab. The generated bulk acoustic wave is steered towards the opposite side with which the sample makes contact and is caused to make one or more internal reflections at the interface between the sample and the quartz before being detected by the receiver on the same side of the generator. The cervical mucus sample in contact with the side of the quartz slab opposite the generating and receiving transducer is being "sampled" by the incident bulk acoustic wave, and the viscosity and temperature information of the sample is imprinted upon the reflected wave through specific modulation of its amplitude.

Because the vaginal probe is made out of plastic with the fused quartz sensing transducer imbedded in it, no current or voltage carrying parts are exposed to the user. There is, therefore, complete electrical isolation between the user and the power source of the probe. The amount of RF power coupled to the vaginal wall near the cervical os during the measurement is less than 100 microwatts, which poses no threats of any kind to the user.

As the device is designed to be inserted into the vagina, this arrangement provides a clean and inert quartz surface, which is smooth and free from any physical attachments such as metallic bonding pads, interconnecting wires or cables or insulating coatings. Moreover, quartz and plastic are good electrical insulators, are inert and can be washed and made sterile. Finally, the viscosity and temperature measurements take only several seconds.

The present invention for the measurement of the rheological property and temperature of biological and other liquids is based on the physical principle that the modulation of the propagation characteristics of ultra-high frequency (UHF) longitudinal or shear bulk waves is affected by the sample liquid when the waves reflect from the liquid at the interface separating the liquid and the medium in which the waves are generated. As explained below, the waves are generated in a quartz medium, and the liquid is against one face of the quartz. The reflection causes both amplitude and frequency shifts.

The sensing transducer of the present invention also utilizes so-called surface acoustic waves (SAW) generation. The surface acoustic waves have combined longitudinal and shear motions coupled by a boundary surface between the solid quartz and the piezoelectric film. In the design of most devices, it is the properties of surface acoustic waves on non-piezoelectric materials such as fused quartz and on piezoelectric materials that are of primary interest.

The dimensions of an interdigital transducer are directly scalable to the frequency of the bulk wave to be excited. Low frequency acoustic waves would require larger dimensions, but for frequencies in the RF range, the dimensions for the transducer are typically only several millimeters. This size lends itself to in situ measurement.

Fused quartz and other media in which the bulk and surface waves propagate have a mechanical impedance. The impedance of an acoustic wave relates the stress associated with the wave to its speed of propagation. The reflection and transmission of bulk waves across interfaces are governed by the respective impedances of the media forming the interface of the angle of incidence of the wave to the interface. Based upon these general physical principles, the sensing transducer of the present invention can take several distinct embodiments, all of which possess a very important characteristic in that they provide an inert, smooth and attachment-free surface on one side of the transducer which is exposable to the liquid or fluid. Because the viscosity of a liquid sample can be characterized by its mechanical or acoustic impedance, the measured modulation on the reflected bulk wave propagation characteristic yields information on the viscosity of the liquid.

In the present invention the same IDT that generates bulk acoustic waves needed for the viscosity measurement in the fused quartz slab also generates surface acoustic waves, which propagate along the surface of the device before reaching the second IDT, which acts as the receiver. If the temperature of the slab changes, the velocity of propagation of the surface acoustic waves changes along with the dimensions of the device, resulting in a change of the phase of the signal exciting the IDT receiver. Thus, a measurement of the change of phase of the surface acoustic wave signal at the IDT receiver with respect to an established reference yields information on the temperature of the slab, and indirectly that of the fluid sample.

DETAILED DESCRIPTION OF THE PREFERRED EMBODIMENT

The Probe

Figure 1:
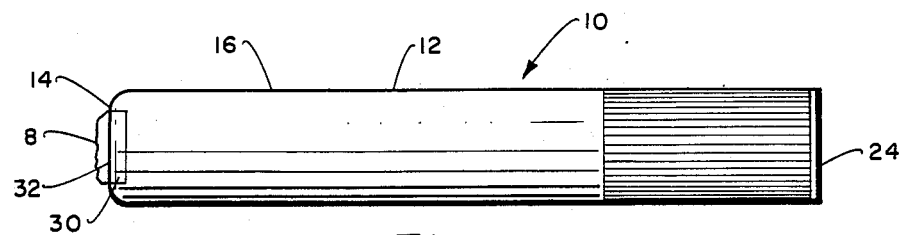
FIG. 1 is a side view of one exemplary embodiment of the ovulation testing apparatus of the present invention.
Figure 2:
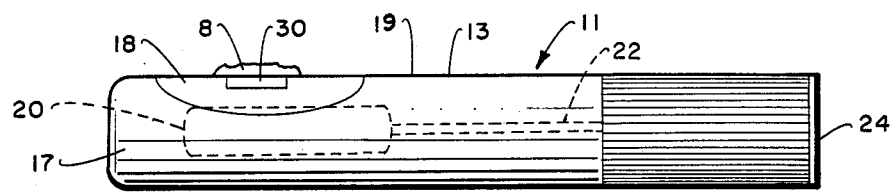
FIG. 2 is a view similar to FIG. 1 showing a variation in mounting the sensor.

Two separate embodiments of the rheological testing apparatus in the form of vaginal probes 10 and 11 are illustrated in FIGS. 1 and 2. The invention is mounted in a generally cylindrical support 12 or 13 made from a physiologically acceptable material. The design of the support causes the testing apparatus to contact the cervical mucus 8. In the preferred embodiment most of either support 12 or 13 is of a thermosetting plastic. The shape can vary for the user's comfort.

The viscosity of cervical mucus 8 (FIGS. 1 and 2), the property of which changes at ovulation, is tested by the apparatus that is positioned against cervical mucus 8 by support 12 or 13. As explained in more detail below, the testing apparatus comprises a slab or substrate 30 which must be positioned so that one face of the substrate is in contact with the cervical mucus. Substrate or slab 30 is shown at either a first location at end 14 of support 12 (FIG. 1), or alternatively, along the cylindrical wall 19 of support 13 (FIG. 2). If slab or substrate 30 is mounted on end 14, it is embedded in the hard plastic end 14 such that its first, outside face 32 (FIG. 1) is flush with the end wall 14 of support 12. In this manner, the front wall presents a smooth surface that will not scratch the delicate tissues involved. Also, a smooth surface can be cleaned more easily.

As an alternative, it may be desirable to have a portion of the cylindrical wall 17 expand to trap cervical mucus between cylindrical wall 17 and the walls of the vagina. FIG. 2 shows a proposed modification to accomplish this goal. A portion 18 of cylindrical wall 17 is formed of an elastic material which normally conforms to cylindrical wall 17. Slab 30 is mounted centrally in portion 18 in such a way that first, front face 32 of slab 30 also conforms to the cylindrical wall 17. Wall 32 of slab 30 is designed to be flat. Whereas, front wall 14 (FIG. 1) is flat so that both front face 32 and front wall 14 can conform with each other, a flat face of slab 32 cannot exactly correspond with cylindrical wall 17 (FIG. 2). Wall 17 and portion 18, therefore, can have a somewhat flat spot, which will not be noticed.

A small air bladder 20 is mounted within support 13 below flexible portion 18. Bladder 20 expands as air is forced into it under pressure through tube 22 to force flexible portion 18 and slab 30 outward against the vaginal wall. The air can be forced through tube 22 through an external pressurized source of air, through a small manual pump mechanism located in handle 24 or in a number of different ways. As an alternative, a cam connected to a shaft to handle 24 could be mounted below elastic portion 18. As the cam is turned, it would force elastic portion 18 upward. Electromechanical devices for causing portion 18 to protrude have also been considered, but it is desirable to limit voltage and current in probe 10.

The placement of the sensor is believed to be important so that it will make contact with the wall of the vagina at or near the cervical os when inserted properly. Other locations for the sensor, however, may be tested and implemented. Supports 12 and 13 are cylindrical in FIGS. 1 and 2, but they may be redesigned to facilitate use and provide comfort.

Probe 10 will house appropriate electronic circuits for generating and receiving the acoustic waves used in the present invention. The power requirements are quite small so the entire unit including the power supplies, a microprocessor, memories and functional and output displays could be on or in probes 12 or 13. As an alternative, the signal processing circuits, power supplies, microprocessor and displays can be mounted in a separate unit. In such a case, electrical connections would run from the probe unit 10 to the central unit.

The Sensing Device

Figure 3:
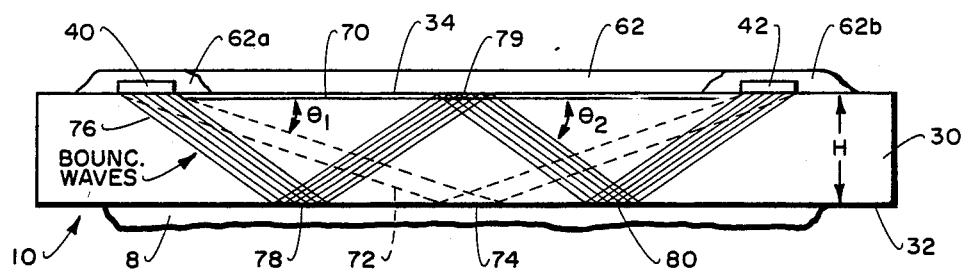
FIG. 3 is a partially schematic sectional view of the quartz substrate or slab of the present invention in side elevation. The figure also shows the wave propagation through the slab in accordance with the present invention.
Figure 4:
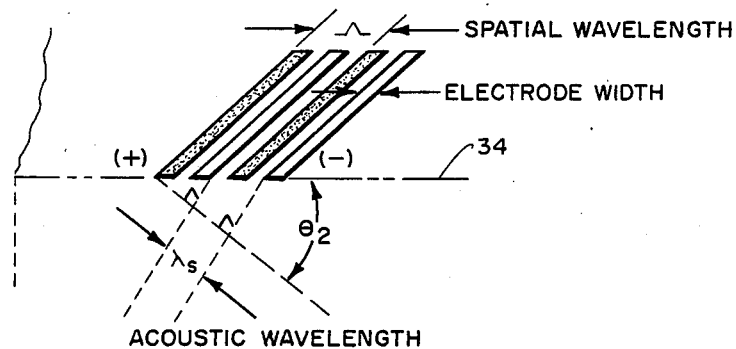
FIG. 4 is a schematic view showing in section one of the two interdigital transducers, of the present invention.

Probe 10 positions slab 30 such that first face 32 is exposable to the fluid to be measured. Two transducers 40 and 42 are mounted on a second face 34 (FIGS. 3-6). One of the two transducers 40 generates a bulk wave toward first face 32. As explained in more detail below, the bulk wave reflects once or preferable at least twice from first face 32 (FIG. 3 shows two reflections) and is received by receiving transducer 42. In the exemplary embodiment, second face 34 is parallel to first face 32, and both the wave generator and receiving transducers 40 and 42 are mounted on second face 34 as explained in greater detail below.

The generating transducer and the receiving transducer are of similar structure in the exemplary embodiment, and both use a uniform interdigital transducer (IDT) which is preferably formed by depositing a metallic electrode structure on a fused quartz substrate. A thin film of a piezoelectric material, zinc oxide (ZnO) 62, in the present embodiment, is deposited on top of the IDTs in order to allow the excitation of acoustic waves in the non-piezoelectric fused quartz substrate.

Figure 5:
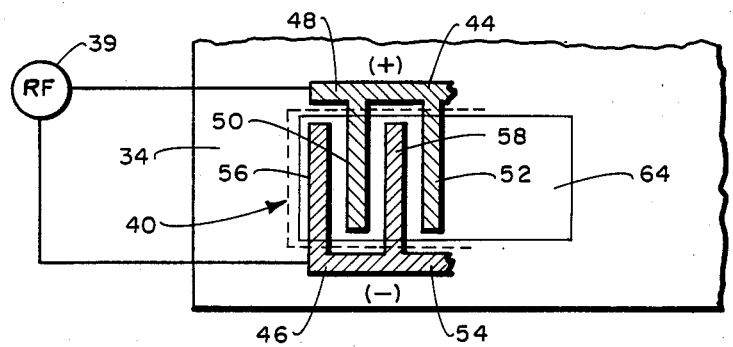
FIG. 5 is a top view of one of the two interdigital transducers of the present invention, which is used to generate or detect acoustic waves.
Figure 6:
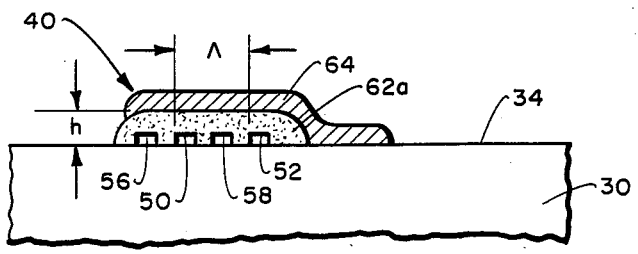
FIG. 6 is a side elevation showing one of the two interdigital transducers of the present invention.

As shown in the exemplary embodiment in FIGS. 5 and 6, the IDT electrode comprises two interspaced combs 44 and 46. Comb 44 has a base member 48 and two depending portions 50 and 52. Base 54 of electrode 46 is spaced from the end of portions 50 and 52 of electrode 44, and portions 56 and 58 extend upward (FIG. 4) from base 54. Their ends are spaced from base 48, and they are laterally spaced from portions 50 and 52. FIGS. 5 and 6 are not to scale, and each electrode in the exemplary embodiment will have many more depending portions 50 and 52 or 56 and 58. See Table 1 below.

When an RF generator 39 applies an electrical potential between the two electrodes 44 and 46, acoustic waves are generated in the quartz substrate.

There are a number of design features incorporated into the structure. To couple the electromagnetic energy into acoustic energy, a layer of piezoelectric material 62 (ZnO in the exemplary embodiment) is deposited over electrodes 44 and 46. A single layer of ZnO may cover both electrodes (FIG. 3) or separate layers 62a and 62b may cover each electrode 44 and 46, respectively (FIG. 3 in phantom and FIG. 6). Metal plate 64 (FIG. 6) covers the ZnO layer 62a to enhance the electromechanical coupling coefficient of the layered structure (ZnO/fused quartz). Without the metal plate 64 the acoustic waves excited in the fused quartz substrate would be very much weaker. The edge of metal plate 64 is attached to substrate 30 beyond the edge of ZnO layer 62a in the desired direction.

The width of the electrodes and their spacing helps determine the propagation of the bulk acoustic waves. Table 1 shows the values of the relevant design parameters for a typical device. See FIG. 4.

TABLE 1

| | |
|---|---|
| Substrate thickness | 0.635 mm |
| Spatial wavelength | 0.025 mm |
| Interdigital transducer electrode pairs | 40 |
| Effective electrode length | 1.520 mm |
| Device size | 6.20 × 4.06 mm |
| Surface wave center frequency | 105 MHz |
| One-bounce angle, $\theta_1$ | 22.3° |
| Two-bounce angle, $\theta_2$ | 39.3° |
| Shear wave wavelength | 0.020 mm |
| Shear wave center frequency | 194 MHz |
| ZnO film thickness | 6.4 microns |
| Metal film thickness | 2,000Å |

The IDT transmitter is designed and spaced from the similar receiver on the same side of the fused quartz slab that the bulk acoustic wave makes exactly two bounces off first base 32 of slab 30 before being received by receiver 42. This wave propagation is shown primarily in FIG. 3. IDT generator 40 generates surface acoustic waves 70 that propogate along the surface or second face of quartz slab 30. More importantly, bulk waves are also generated. A first, one-bounce bulk wave 72 makes only a first reflection at point 74 on first face 32 and reaches IDT receiver 42. The IDT generator 40 also generates a second, two-bounce bulk acoustic wave 76 that makes two reflections 78 and 80 on first face 32 and a second intermediate reflection 79 on second face 34.

Figure 7:
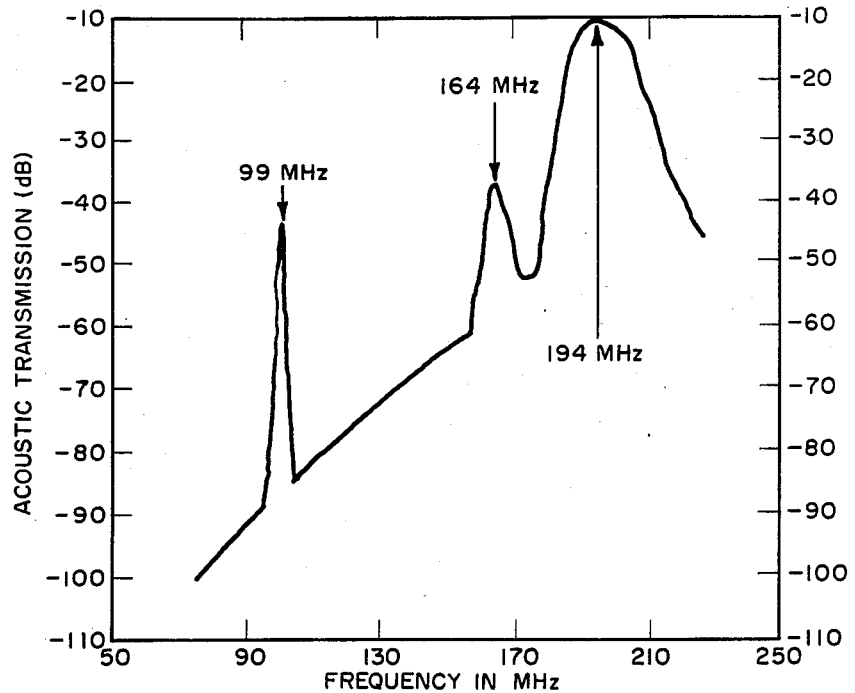
FIG. 7 is a graph showing the acoustic insertion loss as a function of frequency.

FIG. 7 shows the signal loss (received/generated) of the fabricated sensing transducer of the dimensions set forth in Table 1 as a function of the frequency in the RF range. The peak at 99 MHz is due to the surface acoustic wave. The peak at 164 MHz is due to the single reflection bulk acoustic wave 72. The bulk acoustic wave 76 making two reflections as optimized by the design considerations previously discussed causes the strongest peak at 194 MHz.

When liquid samples having various viscosity values at room temperature (22° C.) are placed in contact with first face 32, the detected amplitude for the bulk acoustic wave 76 that makes two reflections (namely at 194 MHz) varies as shown in Table 2, which also shows the actual viscosity.

TABLE 2

| Sample | Viscosity (22° C.) (Centipoises) | Magnitude | Relative Amplitude (dB) |
|---|---|---|---|
| Air | 0 cp | 1.0 | 0 (reference) |
| Ethylene glycol | 20 cp | 0.54 | −5.38 dB |
| Glycerine | 1,490 cp | 0.41 | −7.74 dB |
| Honey | $9.1 \times 10^{15}$ cp | 0.22 | −13.23 dB |

Because the "average" viscosity of human cervical mucus changes from values of several tens of thousands of centipoises during normal times to a low of only a few hundred centipoises during the ovulation period, the device of the present invention is capable of detecting sufficient changes of viscosity values to detect ovulation. Absolute viscosity values assist in predicting the onset of ovulation, but the circuitry necessary to calculate absolute viscosity can be directed to a storage medium so that trends in rate of change of the viscosity values rather than the absolute values can be used for determining the beginning of ovulation.

Viscosity is the principal measurement obtained (using the bulk acoustic waves), but the present invention also can determine temperature of the sensing transducer simultaneously by measuring changes in the phase of the surface acoustic wave (SAW). SAW velocity is a strong function of the temperature of the substrate along which the wave propagates. The temperature can be determined by calibrating the frequency of a resonator set up by the surface acoustic waves as a function of the slab temperature and by monitoring the SAW frequency. Under equilibrium, the temperature of the transducer body should be equal to the temperature of the cervical mucus, which should also be equal to the woman's internal body temperature. The SAW and hence the temperature measurement is not affected by the viscosity measurements. Both principal frequencies for measuring temperature and viscosity can be generated at different times.

Figure 8:
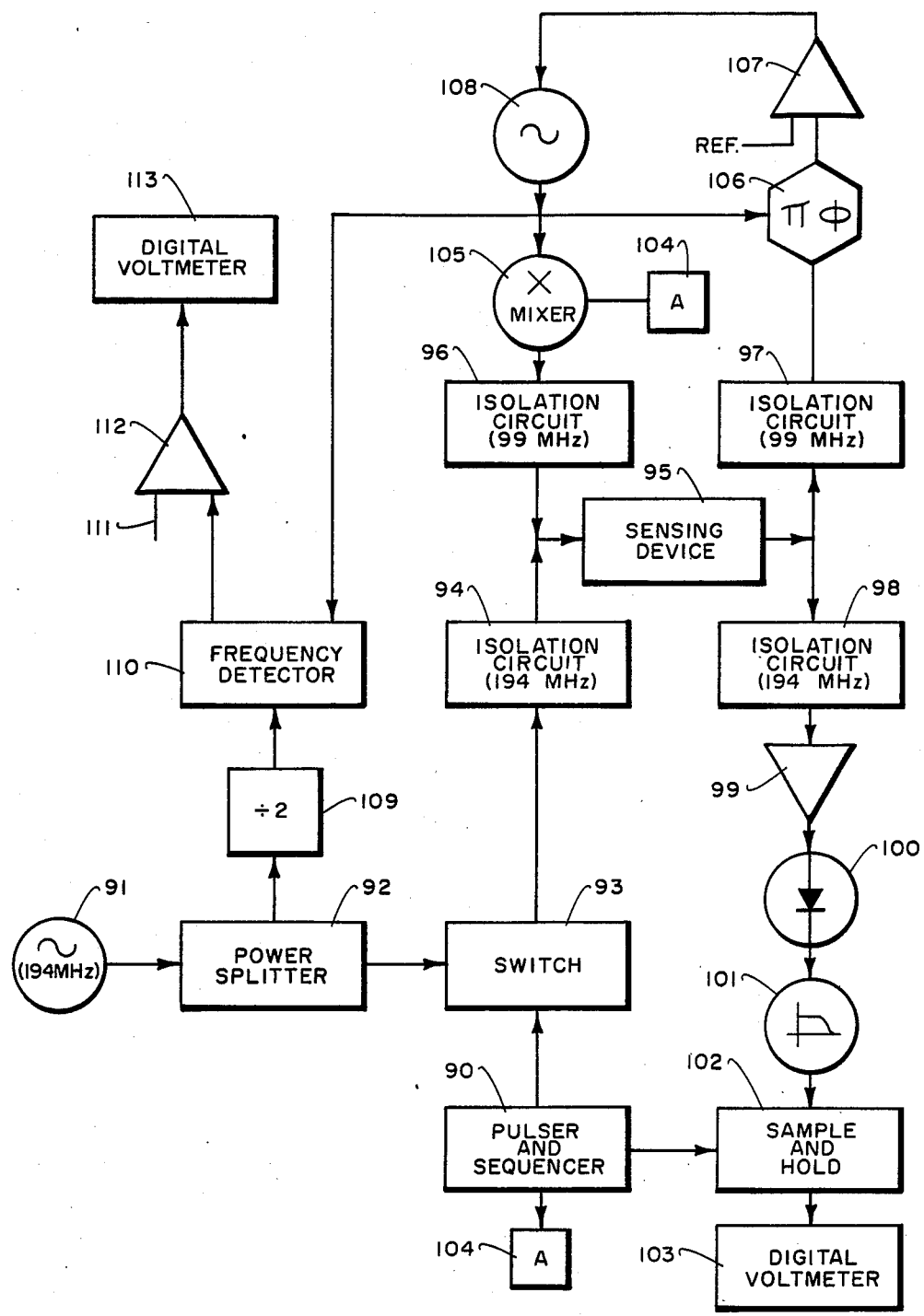
FIG. 8 is a schematic drawing of a circuit design for the time sequential generation and detection of the surface acoustic waves at 99 Mhz and the twice-reflected bulk acoustic waves at 194 MHz measurements, respectively.

A circuit for the time sequential generation and detection of the SAW at 99 MHz and the BAW at 194 MHz for the temperature and the viscosity measurements is shown in FIG. 8. A pulser and sequencer 90 is the main clock and timing keeper of the circuit. A pulse exits the pulser 90 and is used to switch a portion of the free running 194 MHz CW signal originated from a stable oscillator 91 and a power splitter 92. The output of switch 93 is a tone burst (∼0.5 μsec) made out of about 100 cycles of the 194 MHz signal. An isolation circuit 94 allows only the 194 MHz tone burst to go into the sensing device 95 unimpeded. Separate isolation circuits 96 and 97 prevent the 194 MHz tone burst from going into the 99 MHz temperature measurement section of the circuit.

At the output of the sensing device 95 the signal is steered via another isolation circuit 98 to amplifier 99 and is then amplitude detected by the diode detector 100. A low pass filter 101 is then used to condition the signal before its amplitude is measured. The signal of interest that exits the sensing device 95 is delayed by its propagation time through it. Meanwhile the pulser and sequencer 90 sends out another pulse that is delayed from the first excitation pulse (by the delay time through the sensing device) to the sample and hold circuit 102. This delayed pulse allows the sampling of the signal exiting the sensing device. The output of the sample and hold circuit 102, which is a measure of the amplitude of the signal exiting the sensing device, is fed into a digital voltmeter 103 for display and measurement. The amplitude of the signal measured is affected by the viscosity of the fluid in contact with the device. Thus, measurement of the amplitude by this circuit indicates the viscosity of the fluid of interest.

A voltage controlled oscillator 108 operating at a frequency of 99 MHz is the main signal source of the temperature sensing portion of this circuit. The pulser and sequencer 90 sends a pulse from port A 104 into a mixer 105 where it is mixed with the 99 MHz CW signal. The output of the mixer is a long tone burst. The object is to measure the change of phase of this tone burst (a function of the temperature of the device) as it exits the sensing device 95. The pulse used in the mixer 105 is delayed by several microseconds from the early pulses that were used to excite and measure the 194 MHz tone burst used in making the viscosity measurement. The delay of this pulse is determined by the length of time it takes the sensing device to quiet down (multiple reflections, spurious signals) from the earlier excitation. This will not be a problem as the repetition rate of the measurements is of the order of 1 KHz, allowing a length of time of about 1 millisecond for both the simultaneous measurements of temperature and viscosity.

The 99 MHz tone burst goes through the tone isolation circuit 96 and propagates through the sensing device as a surface acoustic wave. At the output of the sensing device the signal goes through another isolation circuit 97 and into a $\pi$ (180°) phase detector 106. Notice that isolation circuit 94 and 98 prevents the 99 MHz signal from going into the 194 MHz section of the circuit. The phase detector 106 is adjusted such that at a reference temperature the output of the phase detector is zero. If the temperature of the device is changed, the phase detector detects the change and its output is compared to a reference in a differential operational amplifier 107. The low frequency output of the operational amplifier is fed back into the voltage control of the voltage controlled oscillator (VCO) 108. The frequency of the oscillator will be changed until the output of the phase detector is zero. Thus, the frequency of the VCO is a measure of the temperature of the device.

The remaining task is to measure this frequency of the oscillator at various temperatures. In this circuit design, the frequency is measured by comparing its value to a reference frequency. The reference frequency has to be close to the frequency of the VCO. A 97 MHz signal as a reference frequency is derived from the divide-by-two circuit 109 from the frequency of the main, stable oscillator used in the viscosity measurement. The reference frequency and the VCO frequency are passed in a frequency detector 110 to measure the difference. At the reference temperature, the offset 111 is adjusted on the differential amplifier 112 such that the output of the differential amplifier, which is fed by the output of the frequency detector and the offset, is calibrated to yield the reference temperature as measured on the digital voltmeter 113. As the temperature of the sensing device 95 changes, the frequency output of the VCO changes and the output of the frequency detector 110 increases. The output of the frequency detector with respect to the offset 111 is compared in the differential amplifier 112 and displayed on the digital voltmeter 113 indicating the new temperature.

Figure 9:
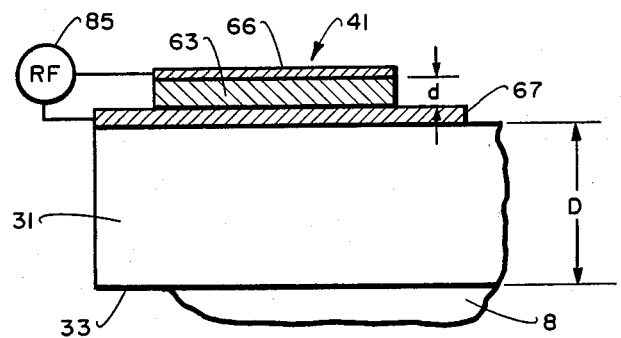
FIG. 9 is a side elevation of an alternative bulk acoustic resonator in accordance with the present invention.
Figure 10:
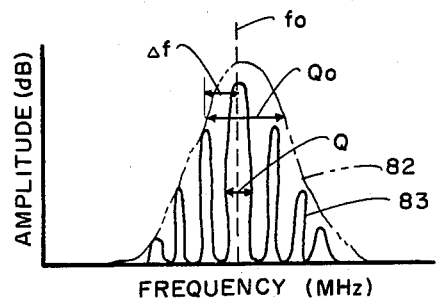
FIG. 10 is a typical frequency spectrum of the bulk acoustic wave resonator device in accordance with the present invention.

FIG. 9 shows a second exemplary embodiment of the sensing transducer 41, which takes the form of a bulk acoustic wave resonator acoustically coupled to a slab of fused quartz. The bulk acoustic wave resonator comprises a thin layer of piezoelectric material 63 such as ZnO sandwiched between two metal electrodes 66 and 67. The electrodes are driven by RF generator 85. The thickness d of the piezoelectric layer 63 determines the resonance frequency $f_o$ of the resonator. FIG. 10 shows a typical frequency spectrum for this type of resonator assuming that the thickness D of the coupled fused quartz slab 31 approaches infinity (curve 82 in phantom). The finesse or $Q_o$ of the frequency spectrum 82 is dependent on the impedance of the ZnO film, its electromechanical coupling coefficient and the impedance of the fused quartz slab 31 (FIG. 9). For finite values of slab 31 thickness D, the frequency spectrum 83 (solid curve in FIG. 10) is modulated into a series of peaks. The separation between the peaks $\Delta f$ is a function of the thickness of D of quartz slab 31. The finesse Q of individual peaks is a function of the coupling loss of the bulk acoustic wave at the first face 33 (FIG. 9) of the fused quartz slab 31 that may or not be in contact with a liquid to be measured. The Q value of the individually modulated peaks changes depending on the mechanical impedance (in this case only the longitudinal impedance) and hence the viscosity of the fluid 8 in contact with the first face 33.

The resonance frequency is a function of the temperature of the ZnO layer 63 and slab 31. Thus, the change in the center frequency $f_o$ upon proper calibration gives the temperature of fluid sample 8 in contact with quartz slab 31.

Figure 11:
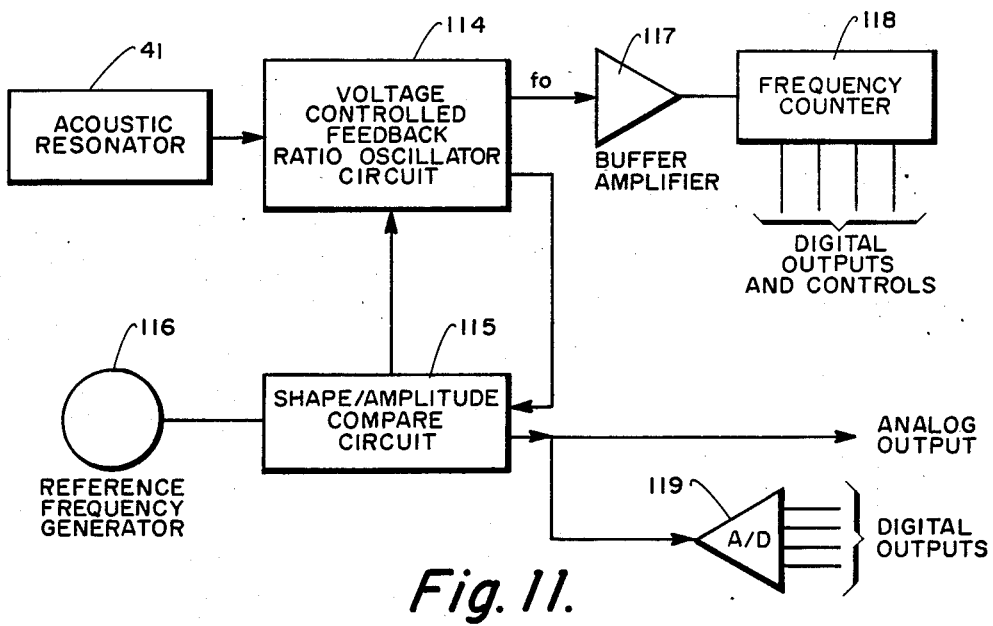
FIG. 11 is a schematic drawing of the circuit design for driving the bulk acoustic resonator device in accordance with the present invention.

FIG. 11 is a schematic diagram of a circuit for measuring the resonant or center frequency $f_o$ and the electrical Q of an acoustic resonator 41. The voltage controlled feedback ratio oscillator 114 is a standard circuit for measuring the resonant frequency of the acoustic resonator 41 comprising a ZnO film 63 deposited on a slab of fused quartz 31 (FIG. 9). The resonance frequency is controlled by the thickness of the fused quartz slab on which the piezoelectric ZnO film is deposited. As the temperature of the fused quartz slab changes, the velocity of an acoustic wave (shear or longitudinal) propagating through it changes. Consequently a measurement of the resonant frequency is a direct indication of the temperature of the fused quartz or the thermal bath (human body) that is in contact with it.

The resonator is set up by having a standing wave or resonance condition in the fused quartz slab, which occurs when an integral number of half wavelengths is set up in the fused quartz slab. The resonance spectrum (FIG. 10) consists typically of several peaks separated by $\Delta f = v/2D$, where v is the acoustic velocity and D is the thickness of the fused quartz slab (FIG. 9).

The shape/amplitude compare circuit 115 measures the two frequencies at which the amplitude of the resonant peak decreases by a factor of 0.707. The difference between the two frequencies yields the so-called "3-dB" bandwidth. The ratio of the resonant frequency $f_o$ to the 3-dB bandwidth gives the electrical Q of the circuit. The shape/amplitude compare circuit 115 is a standard circuit requiring a reference frequency provided by generator 116.

The Q of the resonator is a measure of the energy lost by the resonator. When the ZnO/fused quartz resonator is standing in free space (i.e. with no fluid sample in contact with the first face 33 (FIG. 9)), the Q is determined by the energy lost in the two materials that make up the resonator, namely ZnO and the fused quartz slab. When a fluid sample is in contact with the first surface 33 of the fused quartz slab, some of the energy is lost to the fluid. Consequently the Q of the resonator decreases. Thus a measure of the Q of the resonator yields the amount of energy lost to the fluid, which depends on the impedance of the fluid, which in turn related to the fluid viscosity.

The output of the voltage controlled feedback ratio oscillator circuit 114 is fed to a buffer amplifier 117 before being converted to digital outputs via a frequency counter 118. Similarly, the output of the shape-/amplitude compare circuit can be converted to digital outputs via an analog-to-digital converter 119.

Whereas RF generator 85 is normally driven continuously (FIG. 9), it can also be operated in a pulse-echo mode. In this variation, the RF source 85 generates a tone burst of a given duration. The amplitude variation of these echoes is a function of the mechanical impedance (and hence the viscosity) of the liquid sample 8 in contact with first face 33 of quartz slab 31. By lengthening the duration of the tone burst, the echoes can be made to overlap and interfere with each other. The zero crossing of the resultant interferogram contains the temperature information of the fused quartz slab 31 and liquid sample 8.

Various other modifications and changes may be made in the configuration described above that come within the spirit of the invention. The invention embraces all such changes and modifications coming within the scope of the appended claims.

We claim:

1. A device for measuring fluid viscosity comprising:
   (a) an inert slab having a first face exposable to the fluid;
   (b) acoustic wave generating means on a second face of the slab for generating a bulk wave toward the first face;
   (c) receiving means on the slab in the path of the bulk wave after it reflects from the first face for receiving the reflected bulk wave from the first face and generating a first output;
   (d) first circuit means attached to the receiving means for measuring the amplitude of the first output and comparing the first output to a first reference output whereby the difference between the first output and the first reference output is a function of the viscosity of the fluid in contact with the first face.

2. The device of claim 1 further comprising the generating means generating a surface acoustic wave along the surface of the slab, the receiving means being positioned for receiving the surface acoustic wave and generating a second output; and second circuit means attached to the receiving means for measuring the phase of the second output and comparing the second output to a second reference output whereby the difference between the second output and the second reference output is a function of the temperature of the slab.

3. The device of claim 1 wherein the acoustic wave generating means comprises an interdigital transducer on the second face of the slab opposite the first face.

4. The device of claim 3 wherein the receiving means comprises an interdigital transducer on the second face of the slab.

5. The device of claim 1, wherein the slab is formed of a non-piezoelectric material and the acoustic wave generating means and the receiving means each comprises a pair of electrodes adjacent each other on the second face to which high frequency alternating potential is respectively applied.

6. The device of claim 5 further comprising a layer of piezoelectric material over the electrodes and at least a portion of the slab contacting the electrodes for allowing the excitation of acoustic waves in the slab.

7. The device of claim 6 wherein the piezoelectric material is zinc oxide.

8. The device of claim 6 further comprising a metal plate over the piezoelectric material and the electrodes for enhancing the coupling of the acoustic energy into the slab.

9. The device of claim 8 wherein a portion of the metal plate is connected to the slab.

10. The device of claim 5 wherein each electrode has a base portion and a plurality of arms, each arm extending toward the opposite base and being spaced from the arms of the opposing electrode.

11. The device of claim 10 wherein the width of the arms and the spacing between arms of the opposing electrodes are such that the acoustic wave generating means generates bulk acoustic waves in the slab that reflect first off of the first face, then off of the second face, again off of the first face and then to the receiving means.

12. The device of claim 10 wherein the substrate is about 0.635 mm thick and 6.20 mm long, the distance between adjacent arms on the same electrode is about 0.025 mm, and wherein the device generates waves at about 39.3° to the plane of the first face.

13. The device of claim 1 wherein the slab is formed of non-piezoelectric material, the acoustic wave generating means comprising a first electrode pair on the second face and piezoelectric material on the first electrode pair, and high frequency driving means connected to the first electrode pair for generating acoustic waves in the slab.

14. The device of claim 13 further comprising a metal plate over the piezoelectric material and the first electrode pair for enhancing the coupling of the acoustic energy into the slab.

15. The device of claim 13 wherein the receiving means comprises a second electrode pair of the second face, the device further comprising detecting means connected to the second electrode pair for measuring the amplitude and phase of the acoustic waves propagating through the slab.

16. The device of claim 1 wherein the acoustic wave generating means comprises a first electrode pair of the inert slab and a first oscillator for generating a first signal at a first frequency, first pulse means connected to the first oscillator for converting the first signal into a series of tone bursts, and means connecting the pulse means to the first electrode pair for generating the bulk wave in the inert slab.

17. The device of claim 16 further comprising a second oscillator for generating a second signal at a second frequency, second pulse means connected to the second oscillator for converting the second signal into a second series of tone bursts, and delay means between the first and second pulse means for delaying the tone bursts of the second pulse means to the inert slab.

18. The device of claim 17 further comprising detector means receiving signals from the first oscillator through the inert slab for detecting changes in amplitude of the first signal, the change in amplitude indicating the viscosity of fluid in contact with the device.

19. The device of claim 18 further comprising a phase detector for receiving a signal from the second oscillator through the inert slab for detecting changes in phase of the second series of tone bursts the changes in phase indicating the temperature of the device.

20. The device of claim 1 wherein the acoustic wave generating means comprises resonator means acoustically coupled to the slab for generating waves at a reference freuquency in the slab, the first circuit means receiving output signals from the resonator means and the slab, whereby changes in the amplitude of the first output is a function of the viscosity of the fluid in contact with the first face.

21. The device of claim 20 further comprising frequency detection means associated with the first circuit means for detecting the resonant frequency from the slab, the resonant frequency being a function of the of the temperature of fluid in contact with the slab.

22. A method of measuring the viscosity of a fluid comprising:

(a) placing the fluid on a slab of material;
(b) generating acoustic waves in the slab of material directed at the interface between the slab and the fluid thereby modulating the waves to form reflected waves;
(c) receiving the reflected waves to form a received signal;
(d) comparing the received signal with a known signal received for a viscosity of a given liquid for determining the viscosity of the tested liquid.

23. An instrument for rheological testing of cervical liquid comprising:

(a) a sensing transducer comprising an inert slab having a first face exposable to the liquid, wave generating means on a second face of the slab for generating a bulk wave toward the first face, receiving means on the slab in the path of the bulk wave after it reflects from the first face for receiving the reflected bulk wave from the first wave and generating a first output, first circuit means attached to the receiving means for measuring the amplitude of the first output and comparing the first output to a reference output whereby the difference between the first output and the reference output is a function of the viscosity of the liquid in contact with the first face; and
(b) support means for supporting the sensing transducer with the first face exposable to the cervical liquid, the support means being of a shape for insertion into a vagina for positioning the sensing transducer in contact with the cervical liquid.

24. The instrument of claim 23 wherein the support means includes means adjacent the sensing transducer for expanding the support means for moving the sensing transducer into contact with said cervical liquid.

* * * * *